(12) United States Patent
Ni

(10) Patent No.: US 11,050,223 B2
(45) Date of Patent: Jun. 29, 2021

(54) BIPOLAR IONIZER FOR AIR PURIFICATION AND A DIFFUSER USING THE BIPOLAR IONIZER

(71) Applicant: Shenzhen Yuan Qi Environmental Energy Technology Co., Ltd., Guangdong (CN)

(72) Inventor: Yunshi Ni, Guangdong (CN)

(73) Assignee: Shenzhen Yuan Qi Environmental Energy Technology Co., Ltd., Guangdong (CN)

( * ) Notice: Subject to any disclaimer, the term of this patent is extended or adjusted under 35 U.S.C. 154(b) by 66 days.

(21) Appl. No.: 16/472,126

(22) PCT Filed: Mar. 23, 2018

(86) PCT No.: PCT/CN2018/080245
§ 371 (c)(1),
(2) Date: Jun. 20, 2019

(87) PCT Pub. No.: WO2019/011002
PCT Pub. Date: Jan. 17, 2019

(65) Prior Publication Data
US 2020/0136354 A1    Apr. 30, 2020

(30) Foreign Application Priority Data
Jul. 11, 2017    (CN) .......................... 201710559917.9

(51) Int. Cl.
*H01T 23/00*    (2006.01)
*F24F 8/192*    (2021.01)
*F24F 8/30*    (2021.01)

(52) U.S. Cl.
CPC .............. *H01T 23/00* (2013.01); *F24F 8/192* (2021.01); *F24F 8/30* (2021.01)

(58) Field of Classification Search
None
See application file for complete search history.

(56) References Cited

U.S. PATENT DOCUMENTS 5,746,051 A * 5/1998 Kieser ............... B01D 53/9454
60/275
8,889,079 B2 * 11/2014 Zahedi .................... B03C 3/019
422/171

FOREIGN PATENT DOCUMENTS

| CN | 2277788 | 4/1998 |
|---|---|---|
| CN | 1551432 | 12/2004 |

(Continued)

OTHER PUBLICATIONS

International Search Report, issued in the corresponding PCT application No. PCT/CN2018/080245, dated May 30, 2018, 5 pages.

*Primary Examiner* — Stephen W Jackson
(74) *Attorney, Agent, or Firm* — Hamre, Schumann, Mueller & Larson, P.C.

(57) ABSTRACT

The present disclosure relates to an alternating bipolar ionizer. It is a plate-type structure consisting of a substrate, an emitter plate, a dielectric barrier plate, and a ground plate. The ground plate and the emitter plate form an electric field, and the electrons of the emitter plate are led out of the dielectric barrier plate on a grounding side of the electric field. Some electrons meet the grounding pole plate and flow into the ground plate to form a current, and some escape from the surface of the dielectric barrier plate and meet the indoor air molecules. When the escaped electrons reach a certain rate, the oxygen molecules can be excited to be an ionic state, and air quality can improve. When AC high-voltage current is inputted, the bipolar ions are generated alternately, so a bipolar ionized gas flow can be injected into the air to improve air quality.

16 Claims, 3 Drawing Sheets

(56) References Cited

FOREIGN PATENT DOCUMENTS

| | | |
|---|---|---|
| CN | 107453214 | 12/2017 |
| WO | 2016/121153 | 8/2016 |

\* cited by examiner

BIPOLAR IONIZER FOR AIR PURIFICATION AND A DIFFUSER USING THE BIPOLAR IONIZER

FIELD OF THE INVENTION

The present invention relates to an ionizer, in particular to an alternating bipolar ionizer, and in particular to an alternating bipolar ionizer for air purification.

BACKGROUND OF THE INVENTION

In the prior art, the following structures are mainly used to purify air by gas ionization.

1. Needle tip discharge device (unipolar). Needle tip discharge is the most familiar gas discharge device. Because the needle tip has a small area and a large curvature change, it is the easiest to discharge among the same kind of materials, and therefore it is the mostly and earliest used in the field of electrostatic precipitation. The needle tip was placed in a hexagonal honeycomb array structure in an early stage. Later, it is changed into a round hole structure with a tip, which has obvious effects on dust collection. Because it is unipolar and does not have redox capability, it does not have the function of eliminating odor. As a unipolar generator, whether it is a positive or negative one, it cannot meet the needs of improving air quality. In recent years, carbon fiber bundles have also been used as discharge electrodes. In terms of consistency, they are superior to needle tips, but bundle effects can cause gelation and failure. So is it possible to achieve positive and negative ion excitation on a single needle tip. Experiments have shown that due to the high voltage of AC, a sharp oxidation phenomenon occurs at the needle tip, which quickly blunts the needle tip, making it impossible to continue to discharge and thus causing failure. Therefore, it is difficult to generate bipolar ions in a single needle tip device under normal conditions.

2. A device using a wire to discharge (unipolar). A device that uses a wire (generally a tungsten wire) to discharge generally includes a pair of high voltage (typical power supply configuration is +8150V) tungsten wires, a separator which is located between the high voltage wires and is grounded, and a dust collecting plate (−3650V). This configuration is a unipolar, air-purifying module with electrostatic dust collection as the main function. Due to the uniformity of the diameter of the tungsten wire used, it is impossible to result in rapid passivation by concentrated discharging point. Particles contained in air flow passing through a high voltage generator will be positively charged. It is easy for the particles to be retained in a surface of negatively polarized dust collecting plate when reaching the same plate. This structure is effective. However, it does not have the mechanism for degradation and oxidation of the odor generated by indoor organic volatiles. Therefore, in this type of device, a negative ionizer (generating a small amount of ozone) is often added to a back end to make up for its deficiency.

The above two forms of discharge have a very effective function, which is the visual effect of crushing the aerosol in an instant. Many manufacturers use it as a demonstrator to allow the soot to flow through the generator naturally when thermodynamic expansion rises and then be crushed, letting the observer feel magical and be told that the air has been purified. In fact, the crushed aerosol becomes small particles that the human eye may not be able to observe. In fact, the molecules of any nature have not changed, and the odor has not been eliminated. Therefore, people have been looking for other ways to satisfy the deodorizing effect. For example, add an M-type filter with activated carbon at the back end of an airflow path.

3. Bipolar ionizer with double needle tip (carbon fiber bundle). The generator has two high-voltage ends, DC positive and negative high voltages are applied to the each ends respectively to generate positive and negative ions, respectively. Sharp's purification ion mode would be a typical implementation. Two adjacent emitters each excite their own polar ionic air. Gas molecules or particles with the same polarity charge repel each other (formation of ion wind). If there are gas molecules or particles with opposite polarity charges in the vicinity, they will attract each other and collide with each other to become neutral molecules or particles. This process has an effect on the degradation of organic volatiles, and the energy of the gas and particles colliding with each other participate in the process of oxidative decomposition. For the floating bacteria in the air obtained during the process of mutual attraction, collision and annihilation, the electrolyte in the cell membrane is electrified and killed. For a large number of ionic gas molecules that do not have the opportunity to annihilate with the charge of the opposite polarity, they will be charged after encountering the particles, and the particles will be converted from fly ash to dust. Therefore, the performance of bipolar ionizers with opposite polarity is much better than that of mono-polar ionizers, which is determined by its own mechanism.

SUMMARY OF THE INVENTION

An object of the present invention is to overcome the above-mentioned drawbacks of the prior art, and to provide a bipolar ion alternative generator of a porous or multi-row wire array to inject a bipolar ion gas flow in a living environment, thereby improving indoor air quality.

The technical scheme of the present invention is as follows: a bipolar ionizer for air purification, which is a plate-type structure consisting of a substrate with a thermally conductive sheet, a porous emitter plate, a dielectric barrier plate, and a porous ground plate with ion extraction mechanism all of which are stacked together in sequence.

In the above mentioned bipolar ionizer for air purification, the emitter plate includes a first emitter plate disposed on a top surface of the substrate and a second emitter plate disposed on a bottom surface of the substrate; the dielectric barrier plate includes a first dielectric barrier plate disposed above the first emitter plate, and a second dielectric barrier plate disposed under the second emitter plate; the porous ground plate includes a first ground plate disposed above the first dielectric barrier plate and a second ground plate disposed under the second dielectric barrier plate; the first emitter plate and the second emitter plate are both porous metal sheets; the first ground plate and the second ground plate are both porous metal sheets; an electric field gradient formed between the thermally conductive sheet and the first emitter plate is smaller than an electric field gradient formed between the first emitter plate and the first ground plate, and an electric field gradient formed between the thermally conductive sheet and the second emitter plate is smaller than an electric field gradient formed between the second emitter plate and the second ground plate.

In the bipolar ionizer for air purification, thermally conductive sheet is located at the center of the substrate, and it divides the substrate into two uniform upper and lower pieces; and the first dielectric barrier plate and the second dielectric barrier plate are of the same material and have the same thickness.

In the bipolar ionizer for air purification, the first ground plate and the second ground plate are porous metal sheets of the same structure, and they have meshes regularly distributed in arrays.

In the bipolar ionizer for air purification, the first dielectric barrier plate and the second dielectric barrier plate are made of either high silica glass plates or modified ceramic plates.

In the bipolar ionizer for air purification, thermally conductive sheet is an electric heating sheet.

In the bipolar ionizer for air purification, the periphery of the plate-type structure is provided with a sealing ring.

A diffuser using a bipolar ionizer has a plurality of blades, on which a plurality of the above-described bipolar ionizers are disposed in the same direction.

According to the above technical solution, the ground plate and the emitter plate with the ion extraction structure form an electric field with a precise size, and the electrons of the emitter plate are led out of the dielectric barrier plate on a grounding side of the electric field. A part of the electrons meets the grounding pole plate and flows into the ground plate to form a current, and a part of the electrons escapes from the surface of the dielectric barrier plate and meets the indoor air molecules. When the emitted electrons reach a certain rate, the oxygen molecules can be excited to be an ionic state, and the air quality is improved. When AC high-voltage current is input, the bipolar ions are generated alternately, so that a bipolar ion gas flow can be injected into the air to effectively improve the air quality.

DETAILED DESCRIPTION OF THE INVENTION

Figure 1:
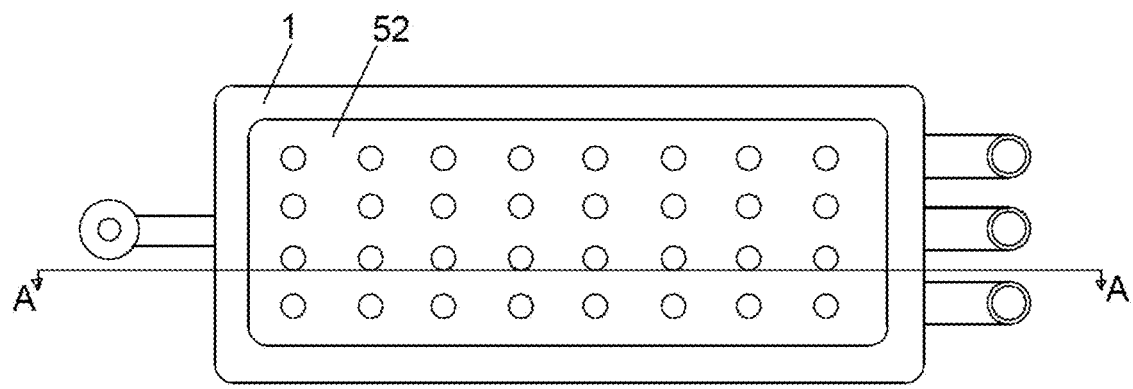
FIG. 1 is a front view of a bipolar ionizer for air purification of the present invention.
Figure 2:
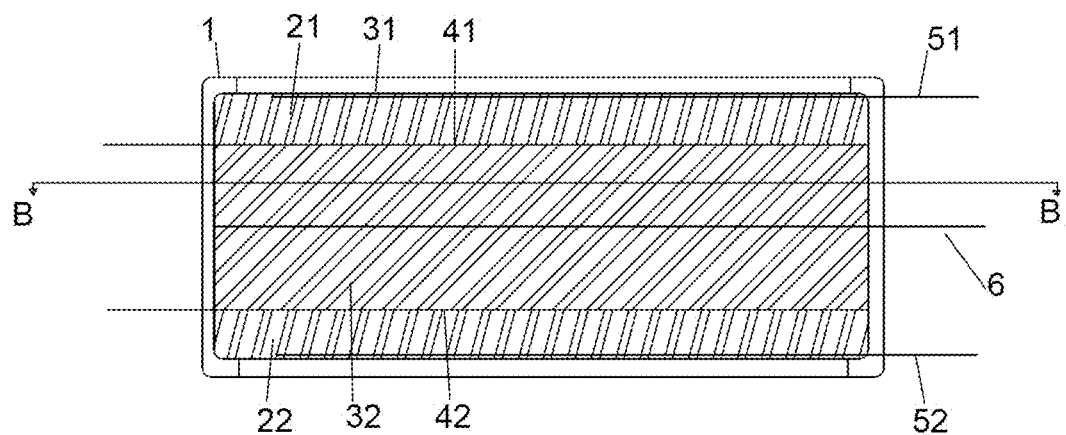
FIG. 2 is a cross-sectional view of a portion A-A shown in FIG. 1.
Figure 3:
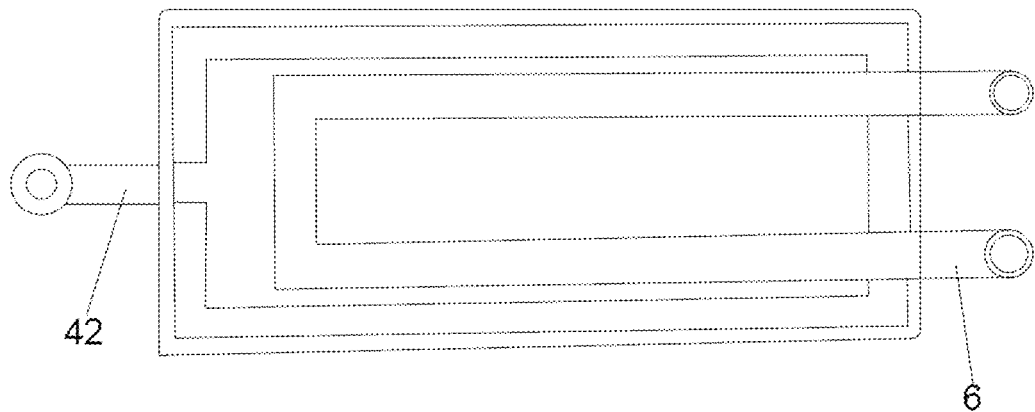
FIG. 3 is a cross-sectional view of a portion B-B shown in FIG. 1.

The present invention will be further described in detail below with reference to the embodiments and the accompanying drawings.

FIGS. 1-3 and 5-6 illustrate an embodiment of a bipolar ionizer for air purification of the present invention. A thermally conductive sheet 6 is located at a center of a substrate 3, and the thermally conductive sheet 6 uniformly divides the substrate 3 into an upper substrate 31 and a lower substrate 32; an emitter plate includes a first emitter plate 41 placed on a top surface of the upper substrate 31 and a second emitter plate 42 placed on a bottom surface of the lower substrate 32. A first dielectric barrier plate 21 is disposed on the first emitter plate 41; a second dielectric barrier plate 22 is disposed under the second emitter plate 42; the first dielectric barrier plate 21 is provided with a first ground plate 51, and the second dielectric barrier 22 is provided with a second ground plate 52; and the first dielectric barrier plate 21 and the second dielectric barrier plate 22 are of the same material and have the same thickness. The bipolar ionizer for air purification is a plate-type structure consisting of a substrate with a thermally conductive sheet 6, a porous emitter plate, a dielectric barrier plate, and a porous ground plate with an ion extraction mechanism all of which are stacked together in sequence. The first emitter plate 41 and the second emitter plate 42 are both porous metal sheets; and the first ground plate 51 and the second ground plate 52 are both porous metal sheets. When the substrate 3 and the first dielectric barrier 21 and the second dielectric barrier 22 are of the same material, the thickness of the substrate 3 is greater than that of the first dielectric barrier 21 and the second dielectric barrier 22, so that the electric field gradient formed between the heat conducting plate 6 and the first emitter plate 41 is smaller than that formed between the first emitter plate 41 and the first ground plate 51. It is ensured that the direction of electron extraction is at a side of the first ground plate 51 and the second ground plate 52, so as to ensure that when the air conditioning system refrigerates, it is possible to generate condensation when its airflow passes through it. The heat conducting plate 6 in the substrate 3 can ensure that electrons escaping from the dielectric barrier material are less disturbed by water molecules and can excite oxygen molecules in the air in their proper energy states.

In this embodiment, the first ground plate 51 and the second ground plate 52 are porous metal sheets having the same structure, and the meshes thereof are regularly arranged in arrays.

In this embodiment, the first dielectric barrier plate 21 and the second dielectric barrier plate are made of either high silica glass plates or modified ceramic plates.

In this embodiment, the thermally conductive sheet 6 is an electric heating sheet.

In this embodiment, the periphery of the plate-type structure is provided with a sealing ring 1.

In the bipolar ionizer of the present invention, since the airflows flowing out from the ionization regions of opposite polarities attract each other, the effect of capturing smaller inhalable particles in the air is better than that of the mono-polar ionized gas, and the effect of capturing inhalable particles of smaller size is more obvious. In the present invention, an ion flow that flows out by the alternating excitation function of the bipolar ions itself has an expansion effect, and the mutual attraction mechanism of the opposite polarity ions causes the ions of opposite polarities to collide sharply outside the outlet. If no gaseous molecules of organic volatiles are encountered in the process, the two are mutually annihilated and returned to the original neutral oxygen molecule state. If it encounters the gaseous molecules of the treated organic volatiles, it is higher than the momentum of the oxygen molecules and the momentum of the two ions, effectively degrades the gaseous molecules of the organic hair, thereby changing its chemical properties. Usually these gaseous molecules will eventually change to gaseous molecules of water and carbon dioxide. Experiments have shown that NS-DBD with bipolar ion alternating excitation function has obvious degradation effect on formaldehyde without any filter and dust collector, and it is also easier to solve the degradation of ammonia/benzene gaseous molecules. The bipolar ionizer of the present invention is effective in killing bacteria in a very short time.

Figure 4:
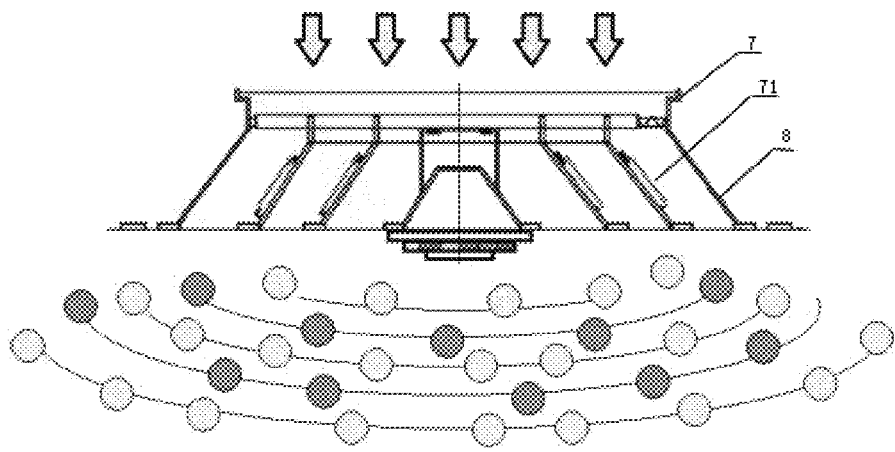
FIG. 4 is a schematic diagram of a diffuser using a bipolar ionizer.

FIG. 4 shows a diffuser using a bipolar ionizer. A plurality of bipolar ionizers 8 are arranged in a same direction on a number of blades 71 of the diffuser 7 and inside an air outlet.

The material of the air outlet is preferably made of non-metal material, so that more air with positive and negative ions can be injected into the indoor space. Bipolar ions can have a higher chance of encountering gaseous molecules/floating bacteria of inhalable particulate matter/organic volatiles in indoor space than net influent air flux. In this sense, the bipolar ionizer is an active purification device.

Figure 5:
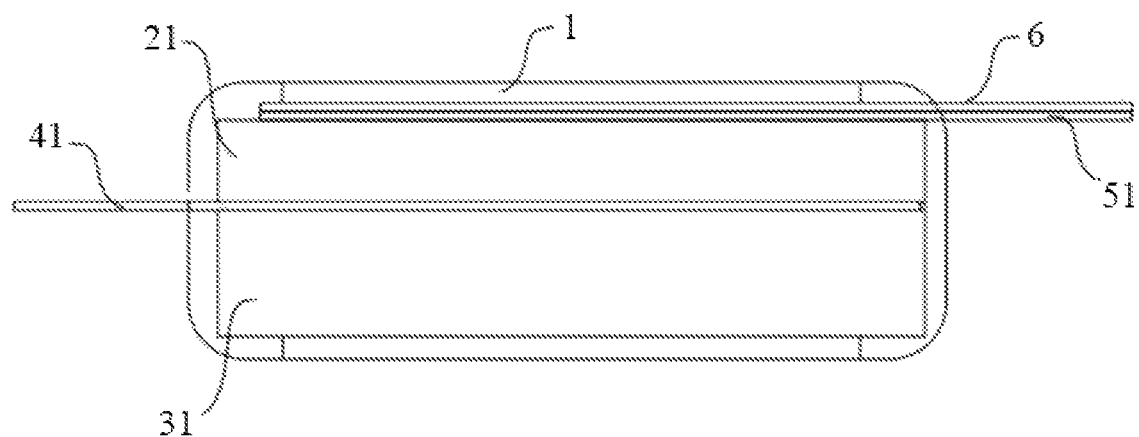
FIG. 5 is a cross-sectional view of a portion A-A shown in FIG. 1.

Referring to FIG. 5, in one embodiment, a thermally conductive sheet 6 may be disposed on a surface of the first ground plate 51 that faces away from the first dielectric barrier 21.

Figure 6:
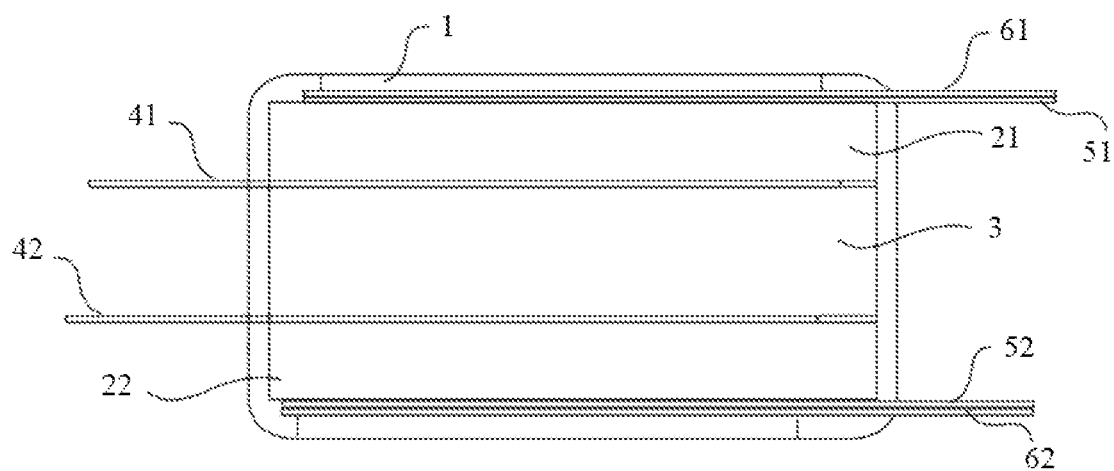
FIG. 6 is a cross-sectional view of a portion A-A shown in FIG. 1.

Referring to FIG. 6, in one embodiment of the bipolar ionizer of the present disclosure may have a first thermally conductive sheet 61 disposed on a surface of the first ground plate 51 that faces away from the first dielectric barrier 21 and a second thermally conductive sheet 62 disposed on a surface of the second ground plate 52 that faces away from the second dielectric barrier 22.

Though various embodiments of the present invention have been illustrated above, a person of the art will understand that, variations and improvements made upon the illustrative embodiments fall within the scope of the present invention, and the scope of the present invention is only limited by the accompanying claims and their equivalents.

The invention claimed is:

1. A bipolar ionizer for air purification, which is a plate-type structure comprising a substrate with a thermally conductive sheet, a porous emitter plate, a dielectric barrier plate, and a porous ground plate with ion extraction mechanism all of which are stacked together in sequence, wherein the porous emitter plate includes a first emitter plate disposed on a top surface of the substrate and a second emitter plate disposed on a bottom surface of the substrate; the dielectric barrier plate includes a first dielectric barrier plate disposed above the first emitter plate, and a second dielectric barrier plate disposed under the second emitter plate; the porous ground plate includes a first ground plate disposed above the first dielectric barrier plate and the second ground plate disposed under the second dielectric barrier plate; the first emitter plate and the second emitter plate are both porous metal sheets; the first ground plate and the second ground plate are both porous metal sheets; an electric field gradient formed between thermally conductive sheet and the first emitter plate is smaller than an electric field gradient formed between the first emitter plate and the first ground plate, and an electric field gradient formed between thermally conductive sheet and the second emitter plate is smaller than an electric field gradient formed between the second emitter plate and the second ground plate.

2. The bipolar ionizer for air purification as recited in claim 1, wherein thermally conductive sheet is located at the center of the substrate, and it divides the substrate into two uniform upper and lower pieces; and the first dielectric barrier plate and the second dielectric barrier plate are of the same material and have the same thickness.

3. The bipolar ionizer for air purification as recited in claim 2, wherein both the first ground plate and the second ground plate have meshes regularly distributed in arrays.

4. The bipolar ionizer for air purification as recited in claim 2, wherein the first dielectric barrier plate and the second dielectric barrier plate are made of either high silica glass plates or modified ceramic plates.

5. The bipolar ionizer for air purification as recited in claim 3, wherein the first dielectric barrier plate and the second dielectric barrier plate are made of either high silica glass plates or modified ceramic plates.

6. The bipolar ionizer for air purification as recited in claim 2, wherein the thermally conductive sheet is an electric heating sheet.

7. The bipolar ionizer for air purification as recited in claim 3, wherein the thermally conductive sheet is an electric heating sheet.

8. The bipolar ionizer for air purification as recited in claim 1, wherein the periphery of the plate-type structure is provided with a sealing ring.

9. A bipolar ionizer for air purification of plate-type structure comprising:
   a substrate;
   a porous emitter plate;
   a dielectric barrier plate; and
   a porous ground plate with ion extraction mechanism, wherein the substrate, the porous emitter plate, the dielectric barrier plate, and the porous ground plate are stacked together in sequence,
   the porous emitter plate includes a first porous emitter plate and a second porous emitter plate;
   the dielectric barrier plate includes a first dielectric barrier plate and a second dielectric barrier plate; and
   the porous ground plate with ion extraction mechanism includes a first porous ground plate and a second porous ground plate, wherein the second porous ground plate, the second dielectric barrier plate, the second porous emitter plate, the substrate, the first porous emitter plate, the first dielectric barrier plate, and the first porous ground plate are stacked together in sequence.

10. A bipolar ionizer for air purification of plate-type structure comprising:
    a substrate;
    a porous emitter plate;
    a dielectric barrier plate;
    a porous ground plate with ion extraction mechanism, wherein the substrate, the porous emitter plate, the dielectric barrier plate, and the porous ground plate are stacked together in sequence; and
    a thermally conductive sheet, wherein the thermally conductive sheet is disposed on a surface of the porous ground plate that faces away from the dielectric barrier.

11. The bipolar ionizer for air purification as recited in claim 9, further comprising:
    a first thermally conductive sheet, wherein the first thermally conductive sheet is disposed on a surface of the first porous ground plate that faces away from the first dielectric barrier;
    a second thermally conductive sheet, wherein the second thermally conductive sheet is disposed on a surface of the second porous ground plate that faces away from the second dielectric barrier.

12. The bipolar ionizer for air purification as recited in claim 9, wherein the first dielectric barrier plate and the second dielectric barrier plate are of the same material and have the same thickness.

13. The bipolar ionizer for air purification as recited in claim 12, wherein both the first porous ground plate and the second porous ground plate have meshes regularly distributed in arrays.

14. The bipolar ionizer for air purification as recited in claim 12, wherein the first dielectric barrier plate and the second dielectric barrier plate are made of either high silica glass plates or modified ceramic plates.

15. The bipolar ionizer for air purification as recited in claim 14, wherein the periphery of the plate-type structure is provided with a sealing ring.

16. A diffuser, comprising a plurality of blades and a plurality of bipolar ionizers as recited in claim 9, wherein the plurality of the bipolar ionizers are respectively arranged in a same direction on said plurality of blades.

* * * * *